United States Patent [19]

Albal et al.

[11] Patent Number: 5,041,680
[45] Date of Patent: Aug. 20, 1991

[54] PRODUCTION OF HYDROGEN PEROXIDE

[75] Inventors: Rajendra S. Albal; Robert N. Cochran; Alan P. Woinsky, all of West Chester, Pa.

[73] Assignee: Arco Chemical Technology, Inc., Wilmington, Del.

[21] Appl. No.: 657,577

[22] Filed: Feb. 19, 1991

[51] Int. Cl.$^5$ .................. C07C 27/00; C07C 45/00
[52] U.S. Cl. ................................ 568/311; 423/591; 568/815
[58] Field of Search ............... 568/311, 815; 423/591

[56] References Cited

U.S. PATENT DOCUMENTS

| 4,975,266 | 12/1990 | Albal et al. | 423/591 |
| 4,994,625 | 2/1981 | Albal et al. | 423/591 |

Primary Examiner—Wayne A. Langel
Attorney, Agent, or Firm—William C. Long

[57] ABSTRACT

Hydrogen peroxide and organic active oxygen-containing compounds in an organic stream, such as that from a methyl benzyl alcohol oxidate after hydrogen peroxide separation, are selectively decomposed by non-catalytic thermal treatment at 150°–180° C. for 20–60 minutes whereby the organic active oxygen materials selectively decompose to acetophenone and methyl benzyl alcohol.

3 Claims, 1 Drawing Sheet

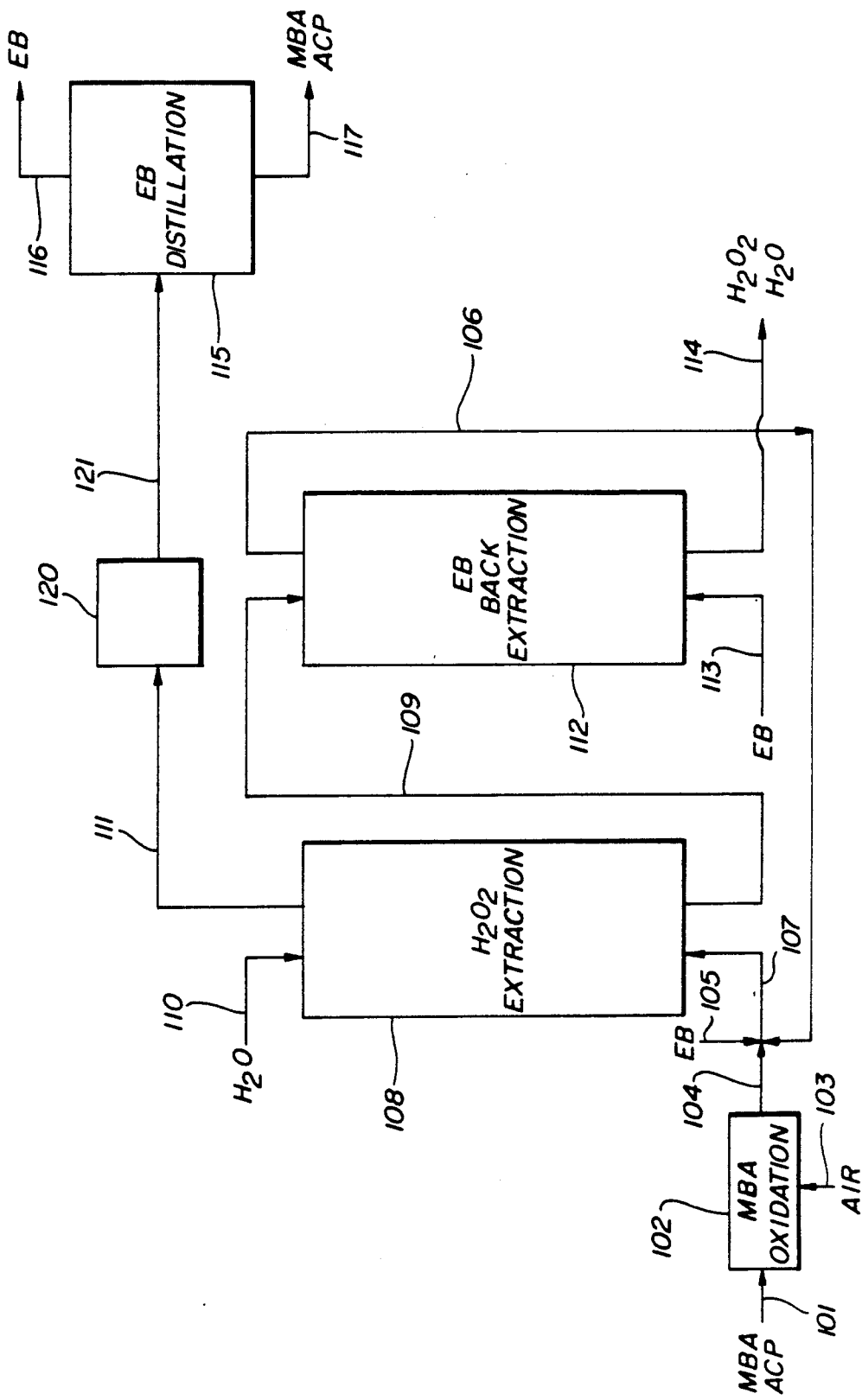

PRODUCTION OF HYDROGEN PEROXIDE

BACKGROUND OF THE INVENTION

1. Field of the Invention

The present invention relates to the production of hydrogen peroxide by the oxidation of methyl benzyl alcohol.

2. Description of the Prior Art

Hydrogen peroxide is an important chemical of commerce which is produced in very large quantities for use in a number of industrial applications. The predominant process used commercially for the production of hydrogen peroxide involves the oxidation of anthrahydroquinone, extraction of hydrogen peroxide and reduction of the resulting anthraquinone to anthrahydroquinone which is reused. This process requires very high capital expenditures in that use of a working solvent with efficient recycle of various process components is necessary.

Substantial efforts have been directed to processes which involve direct combination of hydrogen and oxygen but thus far such processes have not found widespread success.

Hydrogen peroxide has been formed by the oxidation of secondary alcohols. At one time the production of hydrogen peroxide by oxidation of isopropanol was practiced commercially. Other secondary alcohols which have been mentioned as possible starting materials for hydrogen peroxide production include methyl benzyl alcohol and cyclohexanol. See, for example, U.S. Pat. Nos. 2,871,102-4 of Shell Development.

Hydrogen peroxide has also been formed by oxidation of high boiling secondary alcohols such as diaryl methanol, the product hydrogen peroxide being stripped from the reaction mixture during oxidation; see U.S. Pat. No. 4,303,632.

In certain commercial technologies substantial quantities of various secondary alcohols are produced. For example, in the coproduction of propylene oxide and styrene monomer by hydroperoxide epoxidation, methyl benzyl alcohol which is also referred to as alpha phenyl ethanol, 1-phenyl ethanol or methyl phenyl carbinol, is formed and ultimately converted by dehydration to styrene monomer. See U.S. Pat. No. 3,351,635.

An improved process for the production of hydrogen peroxide by the oxidation of methyl benzyl alcohol is described in U.S. Pat. Nos. 4,897,252, granted Jan. 30, 1990 and 4,975,266, granted Dec. 4, 1990.

An improved process for the recovery of hydrogen peroxide from methyl benzyl alcohol oxidation mixtures is described in U.S. Pat. No. 4,897,085, granted Jan. 30, 1990.

During molecular oxygen oxidation of methyl benzyl alcohol to produce hydrogen peroxide with acetophenone as a coproduct, organic peroxidic materials such as ethyl benzene hydroperoxide (EBHP), cumene hydroperoxide, tertiary butyl hydroperoxide (TBHP) and ethyl benzene hydroxyhydroperoxide are formed. It is generally advantageous to separate the bulk of the hydrogen peroxide by water extraction from an organic phase which contains acetophenone and other organics. However, due to the distribution equilibrium between the organic and aqueous phases, a small amount of the hydrogen peroxide and the bulk of the organic peroxidic materials remain in the organic phase.

In certain preferred operations, the acetophenone in the organic phase is hydrogenated to methyl benzyl alcohol which can be recycled to the oxidizer or which can be converted to styrene monomer. For safety reasons as well as to avoid process difficulties such as catalyst deactivation, it is important to decompose active oxygen compounds associated with the acetophenone before further processing. It is also extremely important to ensure that active oxygen-containing compounds are selectively converted to acetophenone and methyl benzyl alcohol in order to avoid uneconomic $C_8$ yield losses.

For removal of trace amounts of $H_2O_2$ from the organic stream, various techniques are practiced in the commercial anthraquinone process for the manufacture of $H_2O_2$. It has been known, for example, that $H_2O_2$ can be catalytically decomposed by various heavy metals such as iron, nickel and copper or noble metals like platinum or palladium. The corresponding metal oxides and hydroxides also act in a similar manner. An essential drawback of this treatment is that the liberated oxygen reacts with hydroquinone present in the solution with renewed formation of $H_2O_2$. Also, in this practice, there is no emphasis given on enhancing the recovery of organic compounds which are recycled.

Treatment with solid substances or substances dissolved in water, which are capable of binding $H_2O_2$ such as sodium hydroxide, sodium metaborate or sodium carbonate has likewise been known. However, the efficiency of this treatment, which is often accompanied by a chemical change, is very low. It has also been suggested to treat organic solutions with mangano- and ferro-compounds, e.g. with a solution of $FeSO_4$ or with alcoholic solution or suspension which contains Fe-$(OH)_2$. However, apart from the consumption of chemicals, such procedures are not satisfactory because manganese or iron enters into the organic solution, and this results in decomposition in the oxidation step. U.S. Pat. No. 3,107,151 describes use of stannous salts like chloride, sulfate or fluoride for $H_2O_2$ decomposition. However, it makes the solution very acidic. U.S. Pat. No. 2,869,989 describes conversion of per-oxygen compounds in the hydrogen peroxide containing oxidation effluent from isopropanol oxidation by thermal treatment of the crude oxidation product at 75° C. to 120° C. for up to an hour.

U.S. Pat. No. 4,994,625, granted Feb. 19, 1991, describes the use of an alumina catalyst to decompose active oxygen constituents in the organic stream which results after separation of hydrogen peroxide from a methyl benzyl alcohol oxidate mixture. Temperatures of 30° to 90° C. are described.

The present invention provides a non-catalytic process for the selective decomposition of hydrogen peroxide and other active oxygen species in an organic stream such as that which results after separation of hydrogen peroxide from a methyl benzyl alcohol oxidate mixture.

SUMMARY OF THE INVENTION

In accordance with the invention, the organic stream containing active oxygen compounds is subjected to non-catalytic, thermal treatment at 150°–180° C. for 20–60 minutes in order to substantially completely decompose the active oxygen constituents without excessive loss of the $C_8$ structure.

BRIEF DESCRIPTION OF THE DRAWING

The accompanying FIG. 1 illustrates in schematic form a suitable embodiment of the invention.

DETAILED DESCRIPTION OF THE INVENTION

U.S. Pat. No. 4,897,085 provides an effective method for the recovery of hydrogen peroxide from methyl benzyl alcohol oxidate reaction mixtures.

In accordance with the process of U.S. Pat. No. 4,897,085, a methyl benzyl alcohol oxidate mixture, which comprises methyl benzyl alcohol, acetophenone and hydrogen peroxide, is admixed with ethyl benzene solvent, and the resulting admixture is extracted with deionized water resulting in an organic phase comprised of the ethyl benzene extractive solvent, methyl benzyl alcohol and acetophenone; and an inorganic phase comprised of hydrogen peroxide in water.

The organic phase from such a separation contains very small but significant amounts of active oxygen-containing materials including hydrogen peroxide, methyl hydroperoxide, ethyl benzene hydroperoxide, ethyl benzene hydroxyhydroperoxide, cumene hydroperoxide and the like. In accordance with the present invention, the organic phase is subjected to a non-catalytic thermal treatment at 150° C.–180° C. for 20-60 minutes, preferably 160°–180° C. for 30-45 minutes, to selectively decompose the active oxygen components, the organic active oxygen-containing materials selectively decomposing to acetophenone and methyl benzyl alcohol.

Referring to the drawing, a methyl benzyl alcohol stream is introduced via line 101 into oxidation reactor 102. Most suitably, the methyl benzyl alcohol stream also comprises acetophenone and represents a process stream available from commercial propylene oxide/styrene monomer technology. Methyl benzyl alcohol is oxidized in reactor 102 by contact with molecular oxygen introduced as air via line 103. Conditions of the oxidation to form hydrogen peroxide and acetophenone are preferably as described in U.S. Pat. No. 4,897,252 and in copending application 07/554,770, filed July 19, 1990.

Liquid reaction mixture is withdrawn from reactor 102 via line 104 and comprises unreacted methyl benzyl alcohol, acetophenone oxidation coproduct as well as such acetophenone as may be present with the methyl benzyl alcohol feed, and hydrogen peroxide product.

Fresh ethyl benzene is introduced via line 105, and recycled ethyl benzene from ethyl benzene back extractor unit 112 is introduced via line 106 and combined with the oxidate mixture. The resulting admixture is passed to the bottom of $H_2O_2$ extractor 108. The light organic phase passes upwardly in 108, countercurrently contacting a heavy aqueous phase passing downwardly from the top, introduced by line 110. A large percentage of $H_2O_2$ contained in the organic feed is extracted into the aqueous stream which exits from below via line 109.

The organic phase, now with most of the $H_2O_2$ product removed, exits 108 from the top via line 111. Contained in this organic phase, as previously mentioned, are small but significant quantities of hydrogen peroxide and organic active oxygen compounds.

The organic phase passes via line 111 to zone 120 wherein it is subjected in accordance with the invention to non-catalytic thermal treatment at 150°–180° C. for 20-60 minutes whereby the active oxygen materials are substantially completely decomposed, the organic materials selectively decomposing to acetophenone and methyl benzyl alcohol. Generally, the thermal treatment is at pressure sufficient to maintain the liquid phase, preferably 150-200 psig.

The mixture from zone 120 passes via line 121 to column 115 wherein it is distilled to separate ethyl benzene overhead via line 116 from the higher boiling methyl benzyl alcohol/acetophenone mixture which is removed via line 117. The ethyl benzene can be recycled to the extraction units or used elsewhere. The methyl benzyl alcohol/acetophenone is especially advantageously dehydrated in accordance with known procedures to form styrene monomer from the methyl benzyl alcohol, followed ultimately by hydrogenation of the acetophenone to produce more methyl benzyl alcohol.

The aqueous hydrogen peroxide phase removed from 108 is sent via line 109 to the top of ethyl benzene back extraction unit 112. The purpose of 112 is to remove and recover dissolved organics in stream 109 by countercurrent extraction with fresh ethyl benzene. The fresh ethyl benzene enters the bottom of extractor 112 via line 113 and travels upwards through the column. The organic product from 112 exits the top via line 106, and is recycled to the organic feed to $H_2O_2$ extractor 108. The purified aqueous hydrogen peroxide phase exits 112 via line 114. If desired, this stream can be treated by conventional procedures to further concentrate and purify the hydrogen peroxide product.

Critical to the present invention is the non-catalytic thermal treatment of the active oxygen organic stream after hydrogen peroxide removal at 150°–180° C. for 20-60 minutes. At temperatures less than 150° C. or with treatment times less than 20 minutes, insufficient active oxygen compound conversion is achieved. Treatment at temperatures above 180° C. or for more than 60 minutes results in poor selectivity to $C_8$ products. Generally, the shorter treatment times are effective at the higher temperature, while the lower temperatures require the longer times. By the process of the invention over 98% decomposition of the active oxygen compounds can be achieved with 75-81% selectivity to $C_8$ products.

The following examples illustrate the invention. Unless otherwise indicated, parts are weights per hour and percentages are by weight.

EXAMPLE 1

100 grams of an organic product stream from the water extractor containing 46.85% methyl benzyl alcohol, 19.14% acetophenone, and 32.27% ethyl benzene, 700 ppm $H_2O_2$, 726 ppm ethyl benzene hydroperoxide, 4037 ppm ethyl benzene hydroxyhydroperoxide, 399 ppm cumene hydroperoxide and 849 ppm other peroxides/hydroperoxides was treated thermally at about 170° C. and 200 psig pressure for 45 minutes under nitrogen atmosphere, analysis of the products stream indicated over 98% decomposition of the active oxygen species with 81% selectivity to $C_8$ compounds. Continuous experiments for over 36 hours at 170° C., 200 psig and 45 minutes residence time also gave good conversion and selectivity.

Comparative Example A 100 grams of an organic product stream from the water extractor containing 53.34% methyl benzyl alcohol, 12.32% acetophenone, 33.35% ethyl benzene, 1,000 ppm $H_2O_2$, 1642 ppm ethyl benzene hydroperoxide, 35.22 ppm ethyl benzene hydroxyhydroperoxide, 436 ppm cumene hydroxide and 797 ppm other peroxides/hydroperoxides was treated thermally at about 140° C. and 200 psig pressure for 60 minutes under nitrogen atmosphere. Analysis of the product stream indicated over 99% decomposition of $H_2O_2$ and 94% decomposition of ethyl benzene hydroxyhydroperoxide. However, only 73.6% decomposition of other peroxides/hydroperoxides, 20% decomposition of cumene hydroperoxide and no decomposition of ethyl benzene hydroperoxide was observed.

Comparative Example B 100 grams of an organic product stream from the water extractor containing 46.06% methyl benzyl alcohol, 18.92% acetophenone, 33.14% ethyl benzene, 400 ppm $H_2O_2$, 1,485 ppm ethyl benzene hydroperoxide, 7,574 ppm ethyl benzene hydroxy hydroperoxide, and 967 ppm other peroxides/hydroperoxides was treated at 190° C. and 200 psi pressure for 30 minutes under nitrogen atmosphere. Analysis of the product stream indicated over 98% decomposition of the active oxygen species with 0% selectivity to $C_8$ compounds.

These comparative examples demonstrate that satisfactory results are not achieved at conditions outside the ranges claimed in accordance with the present invention.

What is claimed is:

1. The process wherein an organic stream containing hydrogen peroxide and organic active oxygen-containing compounds is subjected to liquid phase non-catalytic thermal treatment at 150°–180° C. for 20–60 minutes whereby the said hydrogen peroxide and organic active oxygen compounds are decomposed, said organic active oxygen-containing compounds selectively decomposing to acetophenone and methyl benzyl alcohol.

2. The process of claim 1 wherein the non-catalytic thermal treatment is carried out at 150–200 psig.

3. The process of claim 1 wherein the non-catalytic thermal treatment is carried out at 160°–180° C. for 30–45 minutes.

* * * * *